(12) United States Patent
Marwah et al.

(10) Patent No.: US 6,607,000 B2
(45) Date of Patent: Aug. 19, 2003

(54) FRILLY DENTAL FLOSS

(76) Inventors: Padma Marwah, 6710 Spring Grove Ct., Middleton, WI (US) 53562; Ashok Kumar Marwah, 6710 Spring Grove Ct., Middleton, WI (US) 53562

( * ) Notice: Subject to any disclaimer, the term of this patent is extended or adjusted under 35 U.S.C. 154(b) by 113 days.

(21) Appl. No.: 09/749,337

(22) Filed: Dec. 27, 2000

(65) Prior Publication Data

US 2002/0078973 A1 Jun. 27, 2002

(51) Int. Cl.$^7$ ............................................. A61C 15/00
(52) U.S. Cl. ...................................................... 132/321
(58) Field of Search ................................ 132/321, 329; 428/192, 131, 134, 136, 357, 358, 397, 399, 400

(56) References Cited

U.S. PATENT DOCUMENTS

| 725,081 | A | * | 4/1903 | Hills | 132/329 |
|---|---|---|---|---|---|
| 3,153,418 | A | * | 10/1964 | Fleming | 132/329 |
| 3,511,249 | A | * | 5/1970 | Baitz | 132/329 |
| 3,771,536 | A | * | 11/1973 | Dragan | 132/321 |
| 3,833,972 | A | * | 9/1974 | Brumlik | 24/204 |
| 3,897,795 | A | * | 8/1975 | Engel | 132/321 |
| 4,121,004 | A | * | 10/1978 | Ehrlund | 428/43 |
| 4,265,258 | A | | 5/1981 | Eaton, II | |
| 4,270,556 | A | * | 6/1981 | McAllister | 132/321 |
| 4,277,297 | A | | 7/1981 | Thornton | |
| 4,450,849 | A | | 5/1984 | Cerceo et al. | |
| 4,836,226 | A | | 6/1989 | Wolak | |
| 4,974,615 | A | * | 12/1990 | Doundoulakis | 132/321 |
| 5,063,948 | A | | 11/1991 | Lloyd | |
| 5,130,185 | A | * | 7/1992 | Ness | 428/40 |
| 5,226,435 | A | * | 7/1993 | Suhonen et al. | 132/321 |
| 5,348,153 | A | * | 9/1994 | Cole | 206/361 |
| 5,518,012 | A | * | 5/1996 | Dolan et al. | 132/321 |
| 5,760,118 | A | * | 6/1998 | Sinclair et al. | 524/306 |
| 5,927,299 | A | * | 7/1999 | Rappoport | 132/321 |
| 6,120,895 | A | * | 9/2000 | Kowitz et al. | 428/364 |

* cited by examiner

Primary Examiner—Eduardo C. Robert
Assistant Examiner—David C Comstock

(57) ABSTRACT

A frilly dental floss formed of thin wide ribbon with frilly edge(s) or centrally located slits or the combination thereof, made from a strong, naturally waxy, polymer material preferably from a biodegradable, thin-gauged high-density polyethylene (HDPE) material.

11 Claims, 3 Drawing Sheets

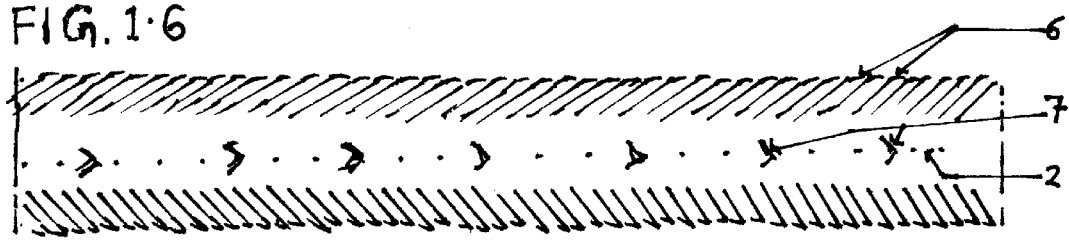
FIG. 1·6
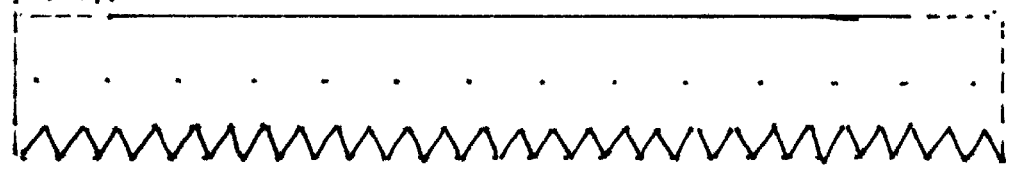
FIG. 1·7
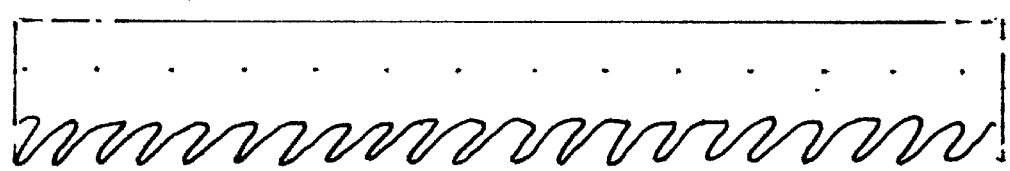
FIG. 1·8
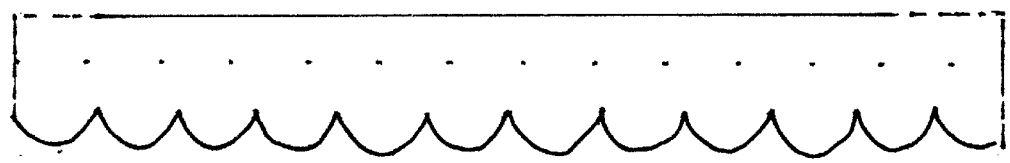
FIG. 1·9
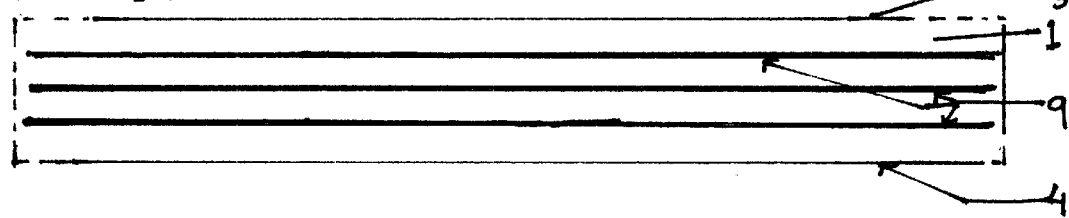
FIG. 1·10

FRILLY DENTAL FLOSS

CROSS REFERENCE TO RELATED APPLICATIONS

Not applicable

STATEMENT REGARDING FED SPONSERED R & D

Not applicable

REFERENCE TO SEQUENCE LISTING, A TABLE, OR A COMPUTER PROGRAM LISTING APPENDIX

Not applicable

FIELD OF INVENTION

The present invention generally relates to the discovery of a new dental floss ribbon with frilly edges, henceforth named frilly floss, a toilet article used to promote dental hygiene by brushing, cleaning and massaging inter-dental spaces of any shape or size.

The present invention filter relates to manufacture of a novel frilly dental floss ribbon having excellent cleaning/plaque removing capability and which is made from an inexpensive plastic polymer preferably from a biodegradable plastic such as high-density polyethylene (HDPE) plastic material Another object of the present invention relates to the discovery of a wide but thin, yet reasonably firm textured floss which is capable of smooth and easy glide into narrowest of dental spaces between the teeth.

A further object of the present invention is to provide a frilly dental ribbon as described and disclosed in this document, which is also capable of filling wide inter-dental pockets, created due to damage of papillary gum tissue or otherwise, to assure quick and proper removal of particles lodged therein.

More particularly the present invention provides a frilly dental floss, with angularly cut edges or centrally located conical slits or combination thereof, as described and disclosed in this document, which is designed to provide easy and unforced entry of floss between inter-dental spaces with minimum proclivity to damage the inter-dental papilla or any part of the gum tissue.

Last but not the least, still another object of the present invention is to provide a dental floss which provides quick and effective brushing and cleaning between the teeth with minimum motion and no special dexterity

BACKGROUND OF THE INVENTION

According to the dental topography, a tooth has two parts; the upper exposed part called crown and the lower root, which is fixed in the gum tissue. Teeth are closely joined together at the crown part leaving a narrow space between them (usually between 0.025 mm to 0.125 mm), but at the gum line, the tapered base of the crown creates a relatively larger space between teeth, which is occupied by the papillary gum tissue (FIG. 2.1). As a result of aging or any kind of gum disease due to the formation of the plaque or tarter, the gum tissues between teeth as well as surrounding the teeth begin to recede and creates more or less a triangular cavity, narrow at the upper sides of the crowns and broad at the gum line. (FIG. 2.2) Tooth-brush generally can not reach such spaces between the teeth but appropriate dental floss or inter dental cleaners are capable of providing cleanliness for such inter dental spaces.

Plaque is the sticky material that develops on the exposed portions of the teeth, consisting of materials such as bacteria, mucus, and food debris. Unremoved plaque eventually mineralizes into a hard deposit called tarter. Formation of plaque and tarter is the main cause of tooth decay and periodontal diseases. Periodontal disease is an infection of the gum tissue surrounding and supporting the teeth. It has been found that, three out of four adults after the age of 35 are affected by some form of gum disease, which is caused by plaque or tarter. Gingivitis, an acute form of gum disease, if treated in its early stage is reversible and can usually be eliminated by daily flossing the teeth.

Dental floss is an inter-dental cleaning article used for dislodging any foreign particle or fiber or food debris from the inter-dental spaces. Conventional dental flosses are usually made up of single or plurality of filaments, which are strands and wind as spools to make a one continuous string. The manufacture of such flosses has often been a lengthy and complicated process. Thickness and small width of the fiber are some of the major drawbacks, which limit effectiveness of such flosses. Many such flosses made from natural or polymeric material are in the form of continuous strands or tape which are very strong but somewhat elastic and hence can be stretched into thinner diameter especially during flossing when user applies force to glide it down between the teeth. This force of action, if applied without great dexterity, can cause the sharpened floss to hit the soft gum tissue with a sudden force causing great discomfort to the user and may injure the gum tissues.

Another drawback with some of the conventional dental floss and their nature to bulk is, when user tries to stretch and force the floss down from upper narrow space to the lower broad space between the teeth, it makes floss very thin. This thinned floss may pass through upper part of the teeth but once it reaches the bottom it can not fill the bottom large space between the teeth and is thus unable to clean the space effectively unless user moves the floss back and forth several times between the teeth. This sawing with the floss to dislodge the food debris may be very harmful and damaging to the tooth at the cementoenamel junction interproximally and may also be damaging to the inter dental papillary gum tissue filing the gingival embrasures, which are shown in FIG. 2.1. The conventional threaded dental floss or their later improved versions such as bristled dental floss or tape type dental flosses are composed of such material, which require lengthy, skilled and often expensive way of manufacturing. The thickness and the fashion of their composition of many improved versions of flosses invented till today, i.e. Eaton, II, U.S. Pat. No. , 4,265,258, issued in 1981, Lloyd, U.S. Pat. No. 5,063,948 issued in 1991, Wolak, U.S. Pat. No. 4,836,226 issued in 1989, Thornton, U.S. Pat. No. 4,277,297 issued in 1981, and U.S. Pat. No. 4,450,849 issued in 1984 to Cerceo, et al., have similar drawbacks and may cause injury and/or bleeding of the gum tissue.

In addition to expensive manufacturing and damage or discomfort which might be caused by such thick dental flosses, another disadvantage has been the insufficiency of cleaning capacity caused, at least in part, by smaller width and smooth surface of the dental floss, (Eaton, II, U.S. Pat. No. , 4,265,258, issued in 1981, Lloyd, U.S. Pat. No. 5,063,948 issued in 1991, Wolak, U.S. Pat. No. 4,836,226 issued in 1989, Thornton, U.S. Pat. No. 4,277,297 issued in 1981, and U.S. Pat. No. 4,450,849 issued in 1984 to Cerceo, et al).

Inventing a tape like dental floss as claimed in the U.S. Pat. No. 4,450,849 issued in 1984 to Cerceo, et al., is in a way improvement but such solution has been inadequate due to difficulty in providing such floss with fine thin texture to be able to pass between closely spaced teeth and in spite of lot of sawing movement of the floss, it still has insufficient cleaning capacity for large inter-dental pockets created as a result of aging and/or due to periodontitis.

Bristled dental floss U.S. Pat. No. 5,063.948 issued to Lloyd, in which inventor utilized multi-filament strand with bristles secured on it by knots. Securing bristles on body of the floss requires a great deal of workmanship, which seems difficult and expensive. The floss and the bristles both require additional stiffening and waxing. Besides, this invention does not improve on the thickness and the diameter of the floss over the conventional flosses and will be difficult to glide through the narrow spaces between the teeth and moreover it cannot fill the large inter-dental spaces.

U.S. Pat. No. 4,265,258 issued to Eaton, II, has similar feature as of Lloyd except that the bristles are not secured on the main strand of the floss by knot. Floss is rather thick, due to multitude of fibers, which are either overlaid or twisted upon each other with a number of fiber ends extending beyond the main body of the floss. Manufacturing of such floss again seems to be tedious and expensive and it has no greater advantage over conventional dental flosses. The length of the extended fiber is very small and they might not be able to provide enough force to dislodge the debris from inter dental spaces between the teeth.

While the foregoing remedial steps have helped in facilitating the flossing to some extent but they have not eliminated or reduced all the drawbacks of the conventional dental flosses. Accordingly, what is needed is a dental floss which is easy to manufacture, quickly and effectively cleans, brushes and massages all shapes and sizes of inter-dental spaces, does not need sawing action to dislodge debris and yet is thin enough to glide down the narrowest spaces between the teeth without applying lot of force or pressure so as to save the soft gum tissue from possible injury.

BRIEF SUMMARY OF THE INVENTION

In fulfillment and implementation of previously recited objects, a primary feature of present invention resides in the provision of a novel dental floss ribbon with frilly edge(s) henceforth called frilly dental floss, which is simple of construction and economical of manufacture. Present frilly floss is a flat thin ribbon made from a non-toxic, naturally waxy plastic polymer, which provides a great combination of strength and economics. The plastic polymer may be further reinforced with strands or thin strips of polymers, when desired.

The frilly floss of the present invention is named so because its edge(s) are cut open into thin strips or similar structures, continually or otherwise, and through the entire length of the floss ribbon. These special angularly cut edges, which may be associated with central small angular slits or centrally located small holes, are important novel features of said invention, and provide a brushing action in the inter dental spaces by providing a safe, gentle quick and effective way to dislodge debris by trapping them into their angular sockets or holes, irrespective of shape or size or width of the dental spaces to be cleaned. The dental floss of present invention thus requires minimum motion (no sawing of the floss) and no special dexterity for cleaning inter-dental spaces. Our thin gauge frilly dental floss is cut in the form of a ribbon with frilly edges invented purposely to provide easy and unforced entry of floss between inter-dental spaces with minimum proclivity to damage the inter-dental papillary gum tissue or any part thereof, while still providing quick and effective brushing and cleaning between the teeth. Another characteristic feature of the present invention lies in its being a ribbon with frilly edge(s) (and not a string) which is capable of filling wide inter-dental pockets, created due to receding papillary gum tissue, to assure quick and proper removal of particles lodged therein.

Our invention provides an easy manufacturing of a novel dental floss article having a completely novel method of cleaning efficiently the spaces of any shape or size between teeth without damaging the soft gum tissue. In addition, the present invention provides a simple, naturally waxy yet gripable, fine textured and last but not the least biodegradable dental floss with its efficient method for smoothly brushing, massaging and cleaning inter-dental spaces. These and other objects and features of the present invention will become more fully apparent from the following description and appended claims, or may be learned by the practice of the invention as set forth hereinafter.

BRIEF DESCRIPTION OF THE DRAWINGS

A frilly dental floss for cleaning spaces between the teeth embodying features of our invention is illustrated in the accompanying drawings, forming part of this application in which FIG. 1 contains various subsections showing representative portions of several of the possible derivations of our dental floss.

FIG. 1.2 shows angularly cut frills on one of the two edges of the floss ribbon.

FIG. 1.3 shows angularly cut frills on both edges of floss ribbon.

FIG. 1.4 shows small conical shaped slits cut in the center of main body of floss ribbon along its central longitudinal axis.

FIG. 1.5 shows angularly cut frills on one of the two edges of floss ribbon together with small conical shaped slits in the center of main body of the floss ribbon.

FIG. 1.6 shows angularly cut frills on both edges together with small conical slits in the center of floss ribbon; the direction of central conical slits being opposite to that of frilly edges on the both sides as shown FIG. 1.7 to FIG. 1.9 show frilly edges created by cutting the edges in some of the various possible shapes such as curves, waves, triangles, half circles etc. These forms as well as thin strips as shown in FIG. 1.2, FIG. 1.3, FIG. 1.5, and FIG. 1.6 may be created along entire length individually or in any combination thereof. Furthermore they may also be created on one or both edges of the floss and in combination with central slits and/or holes in order to enhance the effectiveness of our frilly floss.

FIG. 1.10 shows a perspective flat view of main flat body of the floss ribbon used for making frilly floss, wherein the floss ribbon has been reinforced with thin strands/strips of polymeric material fused or created on it.

FIG. 2.1 shows a perspective view of a person's normal, healthy gums and teeth, where gum and bone anchor teeth firmly in place.

FIG. 2.2 shows a perspective view of a person's dental structure with periodontities, where when plaque and tartar build up and gums begin to recede from the teeth creating triangular inter-dental spaces.

FIG. 3.1 shows passing a flat floss ribbon fully flat or opened and vertically into the spaces between the teeth.

FIG. 3.2 shows accumulation or gathering of floss ribbon at the bottom large pocket space and filling it.

Different parts of various figures are indicated with Arabic numerals in drawings and in the text.

DETAILED DESCRIPTION OF THE INVENTION

Figure 2:
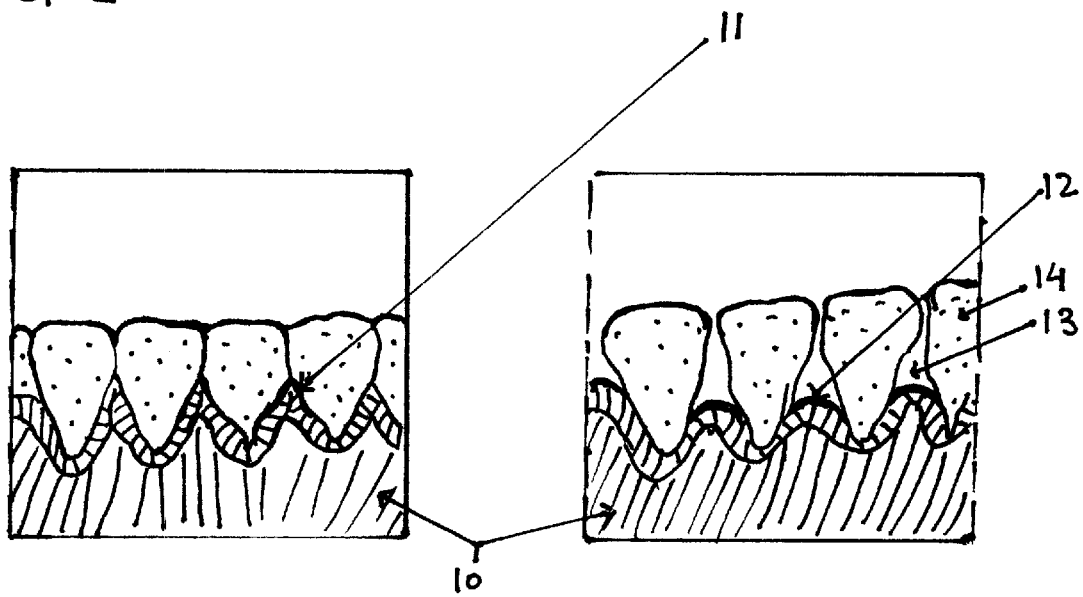
FIG. 2 contains subsections showing topography of the teeth and gum.
Figure 3:
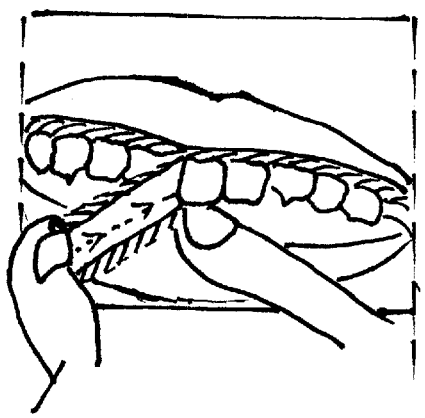
FIG. 3 contains subsections showing a perspective view of flossing action
Figure 3:
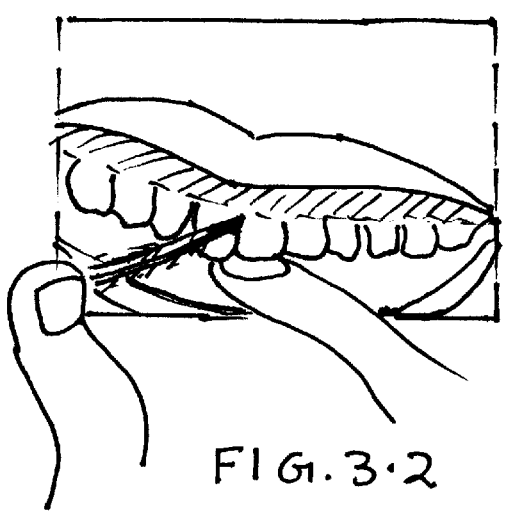

The major drawback of conventional filament floss and flossing is the damage to the gum tissue caused by forceful contact of a dental floss against the gum which often leads to injury and bleeding of the gum and ultimately may cause gum disease. This forceful action is as a result when user tries to push down threaded dental floss, which is relatively thick, through the closely spaced teeth. Besides, smaller diameter/width of the conventional threaded dental floss is not effective in dislodging debris from large inter dental sockets unless user practically uses the floss as a saw in such spaces. This mechanical sawing motion of the threaded floss can be damaging to the tooth at the cementoenamel junction interproximally and also damaging to the inter-dental papillary gum tissue filing the gingival embrasures, which are shown in FIG. 2.1.

This invention relates to the discovery and manufacture of a novel frilly dental floss for cleaning inter-dental spaces of any shape and size as described and disclosed in this document. Our invention of frilly floss utilizes thin-gauged plastic polymer preferably biodegradable such as high-density polyethylene (HDPE) having a thickness of 0.01 mm–0.05 mm, preferably a thickness of 0.01 mm–0.03 mm and more preferably a thickness of 0.015 mm–0.025 mm. From such thin plastic sheets, the invented floss is cut in the form of a ribbon of varying width (0.5 cm–5.0 cm, preferably 0.5 cm–3.5 cm and more preferably 1.0 cm–2.5 cm wide), to be used for cleaning closely spaced teeth as well as large pockets formed at the gum line between the teeth. There are no toxic products evolved either during manufacturing or use or even afterwards i.e. during biodegradation when biodegradable plastic material such as HDPE polymer is used for said purpose. Biodegradable, thin-gauged HDPE plastic is soft, naturally waxy yet perfectly gripable and less flexible and inexpensive polymer. Thus it provides a great combination of economics and strength most suited for the purpose of making dental floss. Currently thin gauged HDPE plastic polymer is being used extensively for making poly bags, which are approved by FDA for food contact.

Our invention of frilly floss is named so because its edges (either or both) are cut open into linear and/or non-linear preferably angular thin strips (1 mm–10 mm deep depending on the width of floss ribbon), continually or otherwise across the entire length of the floss ribbon. Besides, effectiveness of frilly dental floss may be further accentuated by incorporating centrally located small angular slits or holes across the entire central longitudinal axis of the floss, wherein each arm of the conical slit is preferably 1–5 mm long and conical slits are placed about 5 mm to about 30 mm apart. The centrally located small holes, identical or otherwise, are created in any possible shape defined by a closed boundary, such as circles, ellipses, polygons having three or more sides etc. These special angularly cut frilly edges of floss which may be associated with centrally created small angular slits and/or holes, is an important feature which is responsible for cleaning, brushing and massaging action in the inter dental spaces irrespective of shape or size or width of the spaces to be cleaned. It provides a safe, gentle, quick and effective way to trap debris into the angular sockets and dislodge them with little dexterity and less motion (no sawing action of the floss is needed). Our frilly dental floss acts like a rake, which grabs the debris and pulls them out as floss moves against the direction of the frills cut on the edge(s) of the floss. Our frilly dental floss function like an inter-dental brush, and cleans and massages the inter-dental spaces as well as the gums. Another characteristic feature of the present invention lies in its being a wide ribbon (0.5 cm–5.0 cm), which is capable of completely filling wide inter-dental triangular pockets as shown in FIG. 2.2, created due to aging or due to damage of papillary gum tissue. This filling action of our frilly floss is unique and helps in removing and cleaning even large inter dental pockets quickly and efficiently and with out much movement of the floss.

By virtue of being a thin wide ribbon, said frilly floss of the present invention provides an easy and unforced entry of floss even between very narrow inter-dental spaces with minimum proclivity to damage the inter-dental papilla or any part of the gum tissue, while still providing effective brushing and cleaning, with minimum motion and no special dexterity.

Naturally waxy and smooth texture of thin-gauged biodegradable HDPE plastic polymer, when utilized for the purpose, is an additional advantage over the conventional flosses since no extra coating of wax or waxy materials such as Teflon is needed.

Figure 1:
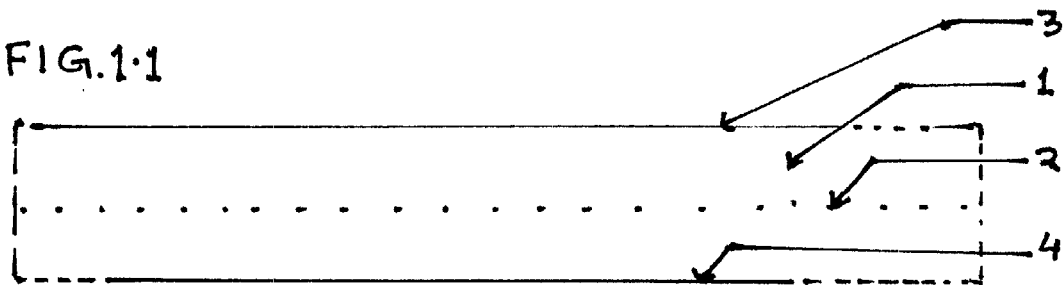
FIG. 1.1 shows a perspective flat view of main flat body of the floss ribbon used for making frilly floss of said invention.
Figure 1:
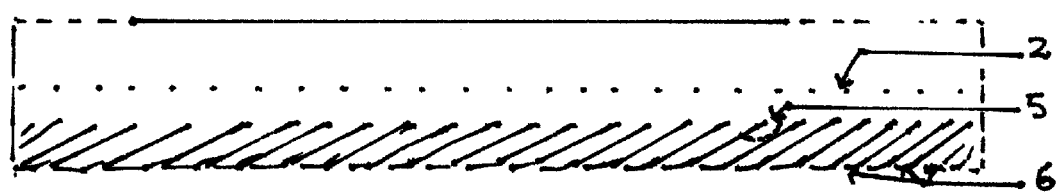
Figure 1:
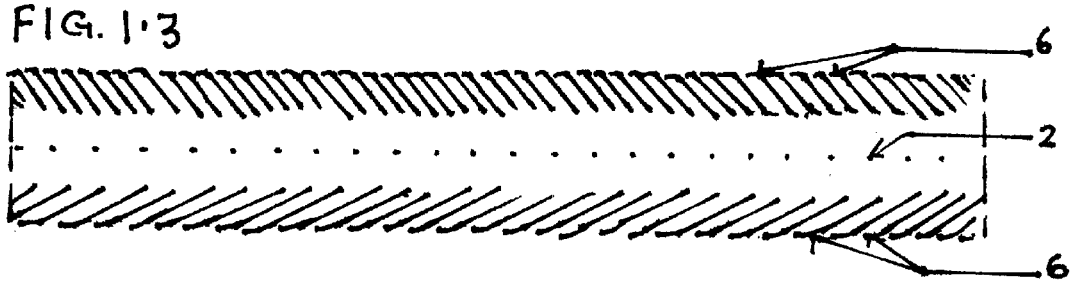
Figure 1:
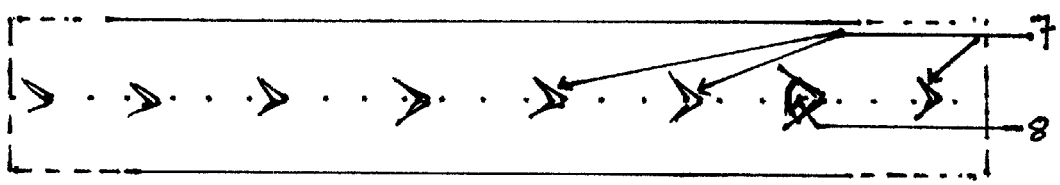
Figure 1:
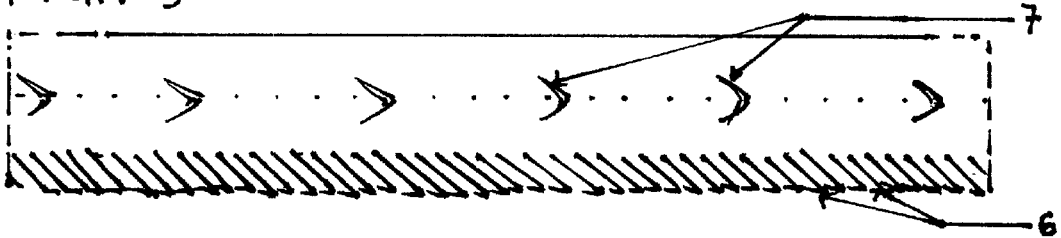

In fulfillment and implementation of previously recited object, a primary feature of the invention resides in the provision of a novel frilly dental floss for cleaning inter dental spaces and for good dental hygiene, and is schematically shown in various subsections of FIG. 1.

FIG. 1 shows several of the possible derivations of our frilly dental floss, FIG. 1.6 being according to the preferred embodiments of the present invention. FIG. 1.2, FIG. 1.3, FIG. 1.4, FIG. 1.5, FIG. 1.7, FIG. 1.8, and FIG. 1.9 are some of the other possible forms of our frilly dental floss.

Dental floss of present invention is comprised of a single piece of ribbon 1 as shown in FIG. 1.1, having a central longitudinal axis 2 and two edges 3 and 4. It is made from a plastic polymer preferably biodegradable, thin gauge (0.01–0.05 mm) high-density polyethylene plastic polymer. Dental floss flat ribbon can be of varying width as defined earlier, and is made so in order to provide effective cleaning for different shapes and sizes of the inter-dental spaces.

The simplest form of our frilly floss as shown in FIG. 1.2 is made simply by cutting one of the edges, either 3 or 4, of the body of the flat ribbon 1 of FIG. 1.1 in the form of strips 6 (FIG. 1.2). The strips 6 are generally cut at an angle 5 (FIG. 1.2) of more than 30° but less than 150°, preferably at an angel of 45±15° and/or 135±15° and more preferably at an angel of 45° and/or 135° as shown in FIG. 1.2. The linear/non-linear angular strips 6 are made 1–10 mm apart, preferably 1–6 mm apart and more preferably 2–4 mm apart, continually or otherwise and across the entire edge of our ribbon floss. The linear/non-linear angular strips are made 1–10 mm deep preferably 2–6 mm deep and more preferably 3–5 mm deep depending upon the width of the floss ribbon Another variation of floss ribbon is further shown in our frilly floss form FIG. 1.3, which is comprised of plurality of angular strips cut straight or otherwise, on its both edges, continually or otherwise, along entire length of said floss. This form of our frilly floss is made by folding body of flat ribbon floss 1 (FIG. 1.1) along its central axis 2, followed by cutting the edges into angular strips 6, at a predefined angle as defined earlier. Once ribbon has been cut on its edges, it can be opened to form said frilly floss of FIG. 1.3.

Another very simple form of floss of present invention is shown in FIG. 1.4. It is comprised of small conical slits 7, cut continually or otherwise, along central axis 2 of said floss ribbon. This is accomplished by folding flat ribbon floss 1 (FIG. 1.1) along its central axis 2, so that both side edges 3 and 4 of said ribbon are closed together, followed by cutting small slits 7 at the folded end of the floss ribbon cut at an internal angle of 60° to 120°, preferably at 90° internal angle, each arm having a length of 1–5 mm and at a distance of 5 m–30 mm along the central longitudinal axis 2 of said floss ribbon. Once the slits have been cut said folded ribbon is opened up to form floss structure of FIG. 1.4.

The effectiveness of said frilly floss is further accentuated by combining frills and slits together into same ribbon floss giving rise to floss structure as shown in FIG. 1.5 and FIG. 1.6 having wide spectrum of cleaning and brushing capabilities. An important feature of frilly floss structure of FIG. 1.5 and FIG. 1.6 is that the direction in which center slits are cut is preferably opposite to the direction in which strips are cut on the edge(s) of floss ribbon. Creating floss in such a manner provides quick and excellent cleaning capability while still retaining proper strength of floss.

The above examples of our frilly floss ribbon are exemplary in nature and in no way binding on the scope of the invention. Frilly edges may be created continually by cutting the edges in any possible shape or form such as curves, waves, inverted triangles, half circles etc. as shown in FIG. 1.7 to FIG. 1.9. These forms may be created along entire edge of the floss, individually or in any combination thereof Furthermore they may also be created in combination with central slits and/or holes in order to enhance the effectiveness of our frilly floss.

FIG. 1.10 shows a perspective flat view of main flat body of the floss ribbon used for making frilly floss, wherein the floss ribbon has been reinforced with strands or thin strips 9 of polymeric material fused or created on it. This strengthened floss ribbon may be used to make frilly floss of various shapes and sizes as described for the floss ribbon of FIG. 1.1.

The proper and appropriate use of the present invention helps in reducing and alleviating the fear of inexperienced as well as experienced persons alike while flossing between the teeth. People with closely spaced teeth and healthy gum or with large triangular pockets as shown in FIG. 2.2 with diseased gum can happily and comfortably take care of their teeth and gums themselves since said invented frilly dental floss assures a great deal of protection against injury and bleeding gums. Besides, persons may save a lot of money by performing dental flossing safely and avoiding the need to seek the help of professionals.

During use, frilly floss is opened completely to form a flat ribbon structure as shown in FIG. 1.1 to FIG. 1.10. A small portion of frilly floss approximately 5–15 inches long, is held tightly between the thumbs and the forefingers of both hands and close to entering side of the edge of the floss, from where floss is guided between the teeth using a gentle rubbing motion. On average, the space between the teeth ranges from about 25 micron (1 mil or 0.025 mm) to about 125 micron (5 mils or 0.125 mm), whereas thickness of our frilly floss ranges from ~10 micron (0.01 mm) to ~25 micron (0.025 mm). This fine and thin texture of frilly floss allows the floss to pass smoothly and without force or pressure, into the inter-dental spaces of the teeth without increasing the space between the teeth and without any damage to the teeth or the gum tissue. Once floss ribbon has reached into the inter-dental space it can be moved in either direction, preferably in the direction in which angular strips are cut on the edges to rake out the debris, or gently move side to side or up and down, a few times to remove all unwanted materials from there.

Once the tight space between the teeth has been cleaned, frilly floss can be moved all the way down to the gum line and to the triangular sockets as shown in FIG. 2.2. There floss ribbon gathers to form a rope like structure, and due to its large width and frilly edges, it is able to fill even large pockets. The small angular slits cut in the center axis of floss and enormous surface area provided by angular strips cut on its edges, act like tiny scoops with brush, which help in loosening and scooping away the debris. A gentle motion either one way or side to side, by said frilly floss is applied to loose, scoop and pull out any small or large amount of material or plaque from within the gingival sulcus area and from the tooth surface.

After inter-dental area and gingival sulcus area have been cleaned, floss is taken out by causing floss to pass back out between the crowns of the teeth away from the gum by slowly pulling floss from its one edge to another so that it comes out as a flat ribbon, or simply by gently pulling the floss completely away from the gum line, from the large pocket areas (FIG. 2.2).

It has been experienced that only few strokes or a small amount of gentle motion by our novel frilly floss is all that is required to dislodge debris and effectively clean any shape or size of inter-dental spaces without damaging or injuring the soft gum tissue. This quick and excellent cleaning capability of our frilly floss is solely due to scoop action of the center slits and angular spaces formed on the frilly edges as well as brushing and massaging action provided by the enormous surface area of the strips created on the edges of the floss.

Our HDPE plastic made frilly dental floss is naturally waxy, smooth and gripable and does not need any extra wax coating, but it can have antibacterial properties or flavoring properties, which are not necessary for cleaning but can be incorporated within the floss ribbon by means known to the polymer art.

The invention has been described with reference to the preferred embodiments and some of the derivation thereof, which are illustrative and not limiting. Various changes may be made without departing from the sprit and scope of the invention as defined in the appended claims.

We claim:

1. A frilly dental floss ribbon, made of a polymer material, for cleaning, massaging between a user's teeth, and removing plaque, the frilly floss comprising a thin flat ribbon having a length, a width, two identical flat surfaces, two edges, and two terminal ends, wherein:
    a) either or both said edges are cut forming frills along either or both said edges of said flat floss ribbon, and
    b) said flat floss ribbon having centrally located small V-shaped slits, in combination with said frills on either or both said edges of said flat ribbon said slits created by cutting said flat surface of said floss ribbon at an internal angle of about 60° to about 120° along the central longitudinal axis of said floss ribbon, each side of said V-shaped slits being about 1 mm to about 5 mm long, and placed about 5 mm to about 30 mm apart along the length of the central longitudinal axis of said flat floss ribbon, said slits defining flaps for loosening and scooping debris out from between a user's teeth.

2. The frilly dental floss as claimed in claim 1 wherein said polymer is a biodegradable polymer.

3. The frilly dental floss as claimed in claim 2 wherein said polymer is a biodegradable, thin-gauged high-density polyethylene polymer.

4. The frilly dental floss as claimed in claim 1 wherein said polymer is reinforced by fusing or creating strands or thin strips of polymer ribbon on the flat surface of said floss ribbon.

5. The frilly dental floss as claimed in claim 1 wherein said dental floss ribbon has a thickness of about 0.01 mm to about 0.05 mm and a width of about 0.5 cm to about 5 cm.

6. The frilly dental floss as claimed in claim 1 wherein either or both edges of said flat ribbon are cut into frills selected from the group consisting of angularly cut strips, semi circles, triangles, and waves.

7. The frilly dental floss as claimed in claim 6 wherein said frills are angularly cut strips, cut about 1 mm to about 10 mm apart at an angle of about 30° to about 150° with respect to the control longitudinal axis and about 1 mm to about 10 mm deep from the edge toward the control longitudinal axis.

8. A frilly dental floss ribbon, made of a biodegradable thin-gauged high-density polyethylene polymer material, the frilly floss comprising a thin flat ribbon having a length, a width, two identical flat surfaces, two edges and two terminal ends, wherein:

a) either or both said edges are cut forming frills along either or both said edges of said flat floss ribbon, and b) said flat floss ribbon having centrally located small V-shaped slits, in combination with said frills on either or both said edges of said flat ribbon said slits created by cutting said flat surface of said floss ribbon at an internal angle of about 60° to about 120° along the central longitudinal axis of said floss ribbon, each side of said V-shaped slits being about 1 mm to about 5 mm long, and placed about 5 mm to about 30 mm apart along the length of the central longitudinal axis of said flat floss ribbon, said slits defining flaps for loosening and scooping debris out from between a user's teeth.

9. The frilly dental floss as claimed in claim 8 wherein said dental floss ribbon has a thickness of about 0.01 mm to about 0.05 mm and a width of about 0.5 cm to about 5 cm.

10. The frilly dental floss as claimed in claim 8 wherein either or both said edges of said flat ribbon are cut into frills selected from the group consisting of angularly cut strips, semi circles, triangles, and waves.

11. The frilly dental floss as claimed in claim 10 wherein said frills are angularly cut strips, cut about 1 mm to about 10 mm apart at an angle of about 30° to about 150° with respect to the central longitudinal axis and about 1 mm to about 10 mm deep from the edge toward the control longitudinal axis.

\* \* \* \* \*